(12) United States Patent
Yue (10) Patent No.: US 11,000,698 B2
(45) Date of Patent: *May 11, 2021

(54) DEVICE AND METHOD FOR CONTROLLING ROTATION OF RADIOTHERAPY EQUIPMENT

(71) Applicant: Shenzhen OUR New Medical Technologies Development Co., Ltd., Shenzhen (CN)

(72) Inventor: Xiaojun Yue, Xi'an (CN)

(73) Assignee: Shenzhen OUR New Medical Technologies Development Co., Ltd., Shenzhen (CN)

( * ) Notice: Subject to any disclaimer, the term of this patent is extended or adjusted under 35 U.S.C. 154(b) by 0 days.

This patent is subject to a terminal disclaimer.

(21) Appl. No.: 15/930,096

(22) Filed: May 12, 2020

(65) Prior Publication Data
US 2020/0276453 A1    Sep. 3, 2020

Related U.S. Application Data (63) Continuation-in-part of application No. 15/961,889, filed on Apr. 25, 2018, now Pat. No. 10,682,526, (Continued)

(30) Foreign Application Priority Data

Oct. 26, 2015  (CN) .......................... 201510702909.6
May 9, 2020   (CN) .......................... 202020764242.9

(51) Int. Cl.
*A61N 5/10*     (2006.01)
*G16H 20/40*    (2018.01)
*G16H 40/60*    (2018.01)

(52) U.S. Cl.
CPC .......... *A61N 5/1048* (2013.01); *A61N 5/1081* (2013.01); *G16H 20/40* (2018.01); *G16H 40/60* (2018.01); *A61N 2005/1074* (2013.01)

(58) Field of Classification Search
CPC .. A61N 5/1081; A61N 5/1074; A61N 5/1067; A61N 5/1045; A61N 5/10;
(Continued)

(56) References Cited

U.S. PATENT DOCUMENTS 7,590,218 B2   9/2009  Scherch et al.
8,242,465 B2   8/2012  Iwata
(Continued)

FOREIGN PATENT DOCUMENTS

CN   1147410   4/1997
CN   1634617   7/2005
(Continued)

*Primary Examiner* — Don K Wong
(74) *Attorney, Agent, or Firm* — Brion Raffoul (57) ABSTRACT

A device and method for controlling the rotation of radiotherapy equipment are provided. The device includes: a detector, configured to detect the rotation of a rotational load of the radiotherapy equipment, and record a rotational deviation amount when the rotational load rotationally deviates; and a controller, configured to generate correction instructions for eliminating the deviation according to the rotational deviation amount when the detector detects the rotational load of the radiotherapy equipment rotationally deviates. The deviation occurred to the rotation of the rotational load is timely corrected by monitoring the actual rotation of the rotational load of the radiotherapy equipment, thereby improving the safety and positioning accuracy of the radiotherapy equipment.

20 Claims, 6 Drawing Sheets

Related U.S. Application Data which is a continuation of application No. PCT/CN2016/100809, filed on Sep. 29, 2016.

(58) Field of Classification Search
CPC ...... A61N 5/01; A61N 5/1048; A61N 5/1084; A61N 5/104; G16H 40/60; G16H 20/40
See application file for complete search history.

(56) References Cited

U.S. PATENT DOCUMENTS

| | | | |
|---|---|---|---|
| 2006/0215813 A1* | 9/2006 | Scherch | A61N 5/1049 378/65 |
| 2012/0165651 A1 | 6/2012 | Yamaya | |
| 2013/0076289 A1 | 3/2013 | Yamaguchi et al. | |
| 2015/0133713 A1* | 5/2015 | Vierlinck | A61N 5/1067 600/1 |
| 2015/0328483 A1 | 11/2015 | Odawara et al. | |
| 2016/0354617 A1 | 12/2016 | Carlsson | |

FOREIGN PATENT DOCUMENTS

| | | |
|---|---|---|
| CN | 101247851 | 8/2008 |
| CN | 102188778 | 9/2011 |
| CN | 102918363 | 2/2013 |
| CN | 202974248 | 6/2013 |
| CN | 103301581 | 9/2013 |
| CN | 103736211 | 4/2014 |
| CN | 104225807 | 12/2014 |
| CN | 105288869 | 2/2016 |
| GB | 2522914 | 12/2015 |
| JP | 2007167411 | 7/2007 |
| JP | 2010246733 | 11/2010 |
| TW | 20143330 | 9/2014 |
| WO | 2015118021 | 8/2015 |

* cited by examiner

DEVICE AND METHOD FOR CONTROLLING ROTATION OF RADIOTHERAPY EQUIPMENT

This application is a continuation-in-part of U.S. application Ser. No. 15/961,889, filed on Apr. 25, 2018, and entitled "device and method for controlling rotation of radiotherapy equipment", which is a continuation of International Application No. PCT/CN2016/100809 filed on Sep. 29, 2016 and entitled "control device and method for rotation of radiotherapy equipment". The International Application claims priority to Chinese Patent Application No. 201510702909.6, filed on Oct. 26, 2015 and entitled "device and method for controlling rotation of radiotherapy device". This application also claims the priority Chinese Patent Application No. 202020764242.9, entitled "a device for controlling rotation of radiotherapy device" filed on May 9, 2020. The entire disclosures of the prior applications are hereby incorporated by reference in their entirety.

TECHNICAL FIELD

The present disclosure relates to the field of automatic control, and in particular to a device and method for controlling the rotation of radiotherapy equipment.

BACKGROUND

For traditional radiotherapy equipment, e.g. head gamma knife, it is usually to control the rotation of a source body and corresponding collimator body therein to open and close the radioactive sources. Obviously, the accuracy of synchronous or asynchronous rotation of the source body and the collimator body affects the accuracy of the actual radiation dose emitted to the patient's lesion, further affects the uniformity control of a dose field.

An existing head gamma knife employs a semi-closed-loop feedback detection technology for controlling the synchronous or asynchronous rotation, and the rotation accuracy of the head gamma knife is monitored through encoders self-contained in a servo motor on the loop. However, this detection method cannot accurately reflect the real-time position of the gamma knife when it rotates, because the motor and the load thereof are composed of a multi-stage transmission chain such as a speed reducer, a gear, etc., and each stage of the transmission mechanism will amplify the rotation error and will eventually reduce the rotation accuracy of the gamma knife.

SUMMARY

The technical problem to be solved by the embodiments of the present disclosure is to provide a device and method for controlling the rotation of radiotherapy equipment, which can monitor the actual rotation of a rotational load of the radiotherapy equipment and timely correct an error or deviation occurred, when the rotation of the rotational load rotationally deviates, to improve the safety and positioning accuracy of the radiotherapy equipment.

In order to solve the above technical problems, an embodiment of the present disclosure provides a device for controlling the rotation of radiotherapy equipment, the device including: a detector, configured to detect the rotation of a rotational load of the radiotherapy equipment, and record a rotational deviation amount when the rotational load rotationally deviates; and a controller, configured to generate correction instructions for eliminating the deviation according to the recorded rotational deviation amount when the detector detects the rotational load of the radiotherapy equipment rotationally deviates.

In order to solve the above technical problems, an embodiment of the present disclosure provides a method for controlling the rotation of radiotherapy equipment, including: detecting the rotation of a rotational load of the radiotherapy equipment, and recording a rotational deviation amount when the rotational load rotationally deviates; and generating correction instructions for eliminating the deviation according to the rotational deviation amount when the deviation of the rotational load of the radiotherapy equipment is detected.

Different from the other art, the device for controlling the rotation of radiotherapy equipment according to the present disclosure performs actual position monitoring on the rotation of the rotational load. The deviation of the rotational load during its rotation is timely corrected by monitoring the actual rotation of the rotational load of the radiotherapy equipment, thereby improving the safety and positioning accuracy of the radiotherapy equipment.

DETAILED DESCRIPTION

This disclosure will be further described in detail below in conjunction with specific embodiments. Obviously, the described embodiments are merely a part of the embodiments of the present disclosure, rather than all the embodiments. All other embodiments obtained by a person of ordinary skill in the art based on the embodiments of the present disclosure shall fall within the protection scope of the present disclosure.

Full-closed-loop monitoring systems and semi-closed-loop monitoring systems are common monitoring methods in the field of automatic control. The semi-closed-loop monitoring system monitors the driving link of a final implementing actuator in the entire system, but not monitoring the final implementing actuator. The full-closed-loop monitoring system monitors the final implementing actuator of the entire system and compensate for the errors caused by any link in the system. For radiotherapy equipment, e.g. a gamma head knife, the rotary part thereof is used as the final actuator. The control accuracy of the rotation is closely related to the uniformity of the dose field of the radiotherapy equipment and the accuracy of the actual dose absorbed by the lesion. Therefore, the radiotherapy equipment can be accurately controlled by using the full-closed-loop monitoring system.

Figure 1:
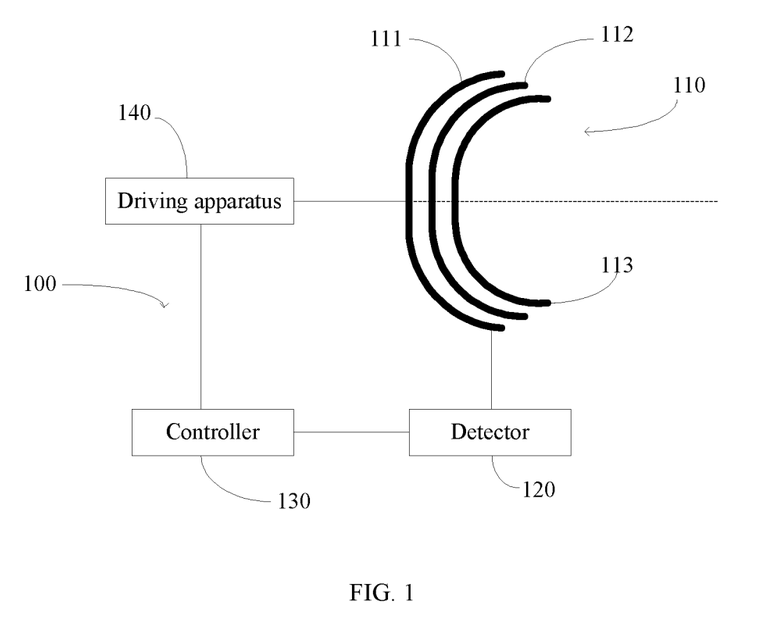
FIG. 1 is a schematic structural diagram of a device for controlling the rotation of radiotherapy equipment, according to a first embodiment of the present disclosure.

Referring to FIG. 1, FIG. 1 is a schematic structural diagram of a device for controlling the rotation of radiotherapy equipment, according to a first embodiment of the present disclosure. The device 100 includes a detector 120, a controller 130, and a driving apparatus 140. Combining with rotational loads 110 of the radiotherapy equipment (not shown), a full-closed loop structure is formed.

In the present embodiment, the rotational loads 110 include, at least, a source body 111, a switch body 112, and a collimator body 113 that are sequentially covered. The source body 111, the switch body 112, and the collimation body 113 are respectively disposed in a bowl-shaped structure, while being rotatable synchronously or asynchronously along a rotation axis perpendicular to the bottom of the bowl structure. The rotation axis may coincide with the rotation shafts of the source body 111, the switch body 112, and the collimation body 113. Since the source body 111, the switch body 112, and the collimator body 113 are sequentially covered, they are considered to rotate along the same rotation axis. The detector 120 is connected to the rotational loads 110 to monitor the rotation of the source body 111, the switch body 112, and the collimator body 113. In some embodiments, the detector 120 employs a circular grating for monitoring. When the rotation of any one or more of the source body 111, the switch body 112, and the collimator body 113 rotationally deviates, rotational deviation amount is monitored/detected by the detector 120 immediately. The detector 120 sends the controller 130 the rotational deviation amount of the source body 111, the switch body 112, and the collimator body 113 when occurs. The controller 130 calculates a deviation correction amount required for normal rotation according to the detected rotational deviation amount, and further sends correction instructions to the driving apparatus 140. The driving apparatus 140 is configured to drive each component of the rotational loads to rotate in a normal state, and correct the rotation of a deviated component according to the correction instructions, to perform a normal rotation.

For the radiotherapy equipment of the present embodiment, the source body 111 is provided with radioactive material for radiotherapy, and the radiation rays are harmful to the human body. However, by controlling the rotation of the source body 111, the switch body 112, and the collimation body 113 very accurately, effective treatment can be achieved, while reducing harm to the medical staff and the patient's healthy tissue. At first, the controller 130 sets the source body 111, the switch body 112, and the collimator body 113 of the rotational loads to rotate at a certain rate and direction, so that the irradiation of the radioactive rays is emitted to the patient according to the treatment plan. During the treatment process, the detector 120 monitors the rotation status of the source body 111, the switch body 112, and the collimator body 113 in real time, and the extension line along the rotation axis of the source body 111, the switch body 112, and the collimator body 113 is perpendicularly passing through an annular center of the detector 120. When the rotation of one or more of the source body 111, the collimator 112, and the switch body 113 rotationally deviates, the rotation axis thereof is also deviated relative to original rotation axis with deviation. It should be noted that the deviation according to the present disclosure includes directional deviation and positional deviation. The detector 120 monitors the respective rotational load 110 which rotationally deviates and sends the corresponding rotational deviation amount to the controller 130. The controller 130 sends correction instructions to the driving apparatus 140, wherein the correction instructions are instructions to eliminate the deviation when the rotation of any one or more of the source body 110, the switch body 120, and the collimator 130 rotationally deviates. The driving apparatus 140 drives the corresponding parts to move according to the correction instructions, for eliminating the deviation and recovering a normal rotation.

Different from conventional arts, the device for controlling the rotation of radiotherapy equipment according to the present disclosure performs actual position monitoring on the rotation of the source body, the collimator, and the switch body of the gamma head knife rotating equipment. The deviation for the corresponding rotation axis is detected during the synchronous or asynchronous rotation. As such, by monitoring the actual rotation of the rotating part of the radiotherapy equipment, it is timely corrected when the rotation of any one of the source body, the collimator, and the switch body rotationally deviates, thereby improving the safety and positioning accuracy of the radiotherapy equipment.

Figure 2:
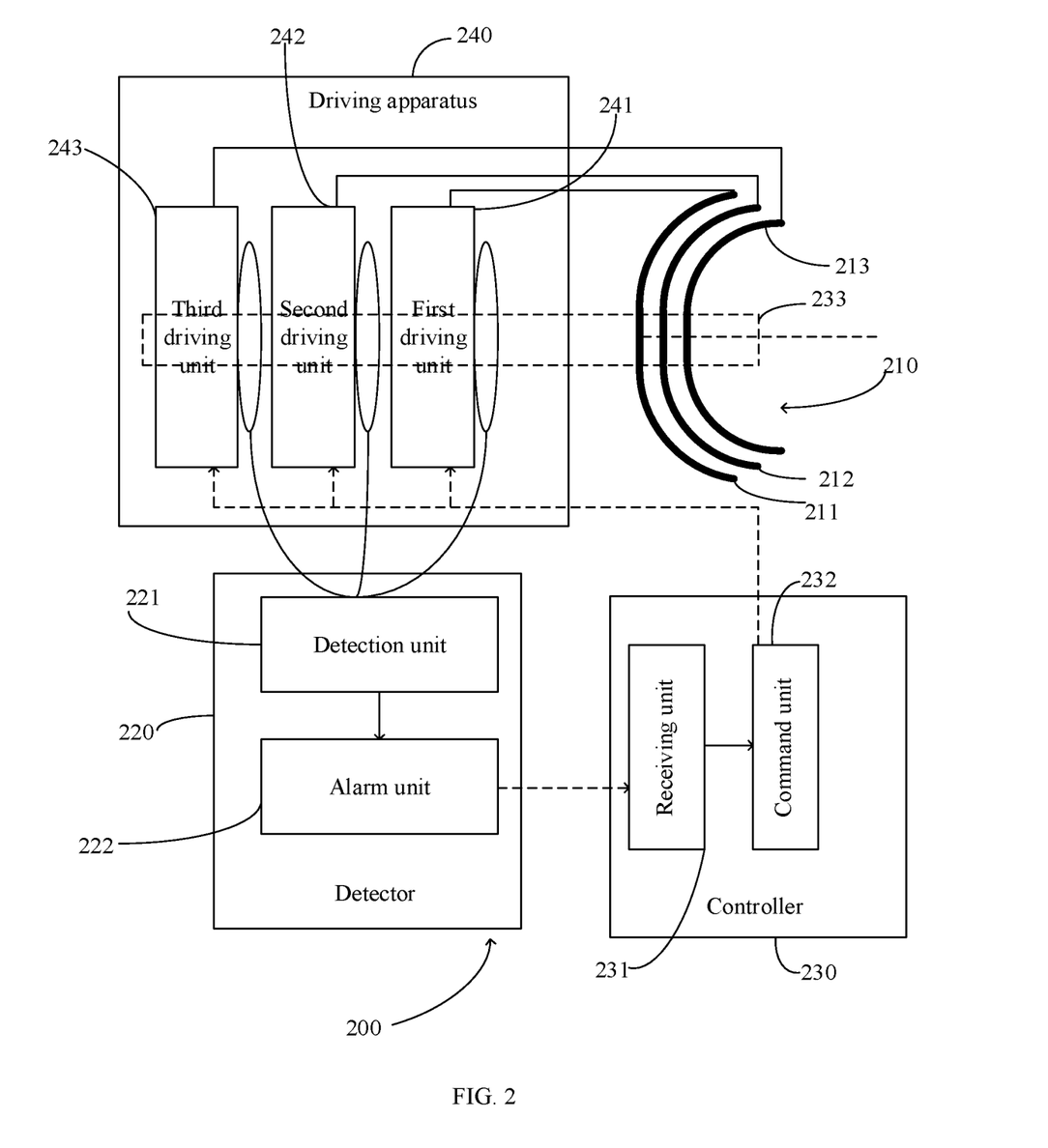
FIG. 2 is a schematic structural diagram of a device for controlling the rotation of radiotherapy equipment, according to a second embodiment of the present disclosure.

Referring to FIG. 2, FIG. 2 is a schematic structural diagram of a device for controlling the rotation of radiotherapy equipment, according to a second embodiment of the present disclosure. The device 200 includes a detector 220, a controller 230, and a driving apparatus 240. The device 200 and rotational loads 210 of the radiotherapy equipment (not shown) form a full-closed loop structure.

The rotational loads 210 include, at least, a source body 211, a switch body 212, and a collimator body 213 that are sequentially covered. The source body 211, the switch body 212, and the collimation body 213 are respectively in a bowl-shaped structure, while being rotatable synchronously or asynchronously along rotation shafts perpendicular to the bottom of the bowl structure. The source body 211, the switch body 212, and the collimator body 213 are sequentially covered and rotated by using rotation control technique. When in use, the source body 211, the switch body 212, and the collimation body 213 are components of the radiotherapy equipment for directly emitting radiation to treat the patient. Through controlling the relative rotation of the three loads, the source radioactive emission is accurately controlled to be opened or closed, according to a predetermined treatment plan. In opposite, if the relative rotation of the source body 211, the switch body 212, and the collimator body 213 rotationally deviates without control, a medical accident will occur.

The detector 220 is configured to monitor the rotation of the source body 211, the collimator 212, and the switch body 213, including a detection unit 221 and an alarm unit 222. The detection unit 221 of the detector 220 is configured to detect the rotation of the axis of the rotation shafts of the source body 211, the switch body 212, and the collimator body 213. When the rotation of any one or more of the source body 211, the switch body 212, and the collimation body 213 rotationally deviates, the detection unit 221 of the detector 220 records the rotational deviation amount detected by the detector 220. In the present disclosure, the rotational deviation amount referred to herein includes a positional deviation and an angular deviation. The positional deviation refers to the positions of the axis of rotation shafts of the source body 211, the switch body 212, and the collimator body 213 are deviated from the initial positions of the axis of the rotation shafts in a parallel direction. The angular deviation means that the rotation shafts of the source body 211, the switch body 212, and the collimator body 213 no longer perpendicularly pass through the annular surface of the detector 220, but with certain angles relative to the vertical direction. When any one or more of the source body 211, the switch body 212, and the collimator body 213 are deviated while in rotational movement, the alarm unit 222 receives the detected rotational deviation amount, issues an alarm signal, and notifies the controller 230 of the rotational deviation amount. The rotational deviation amount detected by the detector 220 is included in the alarm signal. In the present embodiment, a circular grating is used in the detector, which is capable of accurately feeding back the rotational deviation amount and digitally control the axis of the rotation shafts of the source body 211, the switch body 212, and the collimator body 213, so that the actual position of the rotation shafts is strictly controlled at any time, ensuring that the rotation of the source body 211, the switch body 212, and the collimator body 213 has high accuracy both in the dynamic-state and steady-state. When the positional deviation or angular deviation occurs in the source body 211, the switch body 212, or the collimator body 213, the rotational deviation amount thereof can be accurately captured by the circular grating, and the controller 230 is notified of the subsequent corrections.

In this embodiment, before performing the detection by the detector 220, the controller 230 sets a reference rotation axis 233 parallel or being overlapping to the rotation shafts of the source body 211, the switch body 212, and the collimator body 213. The reference rotation axis 233 is virtual and cannot be observed by human eyes, and the position of the reference rotation axis 233 is fixed. Through the reference rotation axis 233 parallel to the axis of the rotation shafts of the source body 211, the switch body 212, and the collimator body 213, the rotation shafts of the source body 211, the switch body 212, and the collimator body 213 are eventually parallel or even overlap.

The controller 230 includes a receiving unit 231 and a command unit 232. The receiving unit 231 of the controller 230 receives the alarm signal and obtains the rotational deviation amount according to the alarm signal. The command unit 232 generates correction instructions according to the rotational deviation amount. The correction instructions are generated according to the rotational deviation amount included in the alarm signal. The correction instructions include the deviation correction amount needed to resume the normal rotation according to the calculated rotational deviation amount of the one or more rotational loads 210, which is calculated by the controller 230. After the correction instructions are generated, the command module 232 transmits the correction instructions to the driving apparatus 240.

The driving apparatus 240 includes a first driving unit 241, a second driving unit 242, and a third driving unit 243. The first driving unit 241, the second driving unit 242, and the third driving unit 243 respectively drive the source body 211, the switch body 212, and the collimator body 213 to rotate. The driving apparatus 240 is powered by a power source (not shown). Upon receiving the correction instructions transmitted by the command unit 232, the first driving unit 241, the second driving unit 242, and the third driving unit 243 simultaneously parse the correction instructions to obtain the deviation correction amount of the corresponding source body 211, the switch body 212, and the collimator body 213. And, the deviation is eliminated according to the deviation correction amount in the correction instructions, and the normal rotation is resumed.

Further, the detector 220 is respectively disposed inside the first driving unit 241, the second driving unit 242, and the third driving unit 243. In this embodiment, the detector 220 includes the circular grating, and the circular grating is a ring-shaped structure. The rotation shafts of the source body 211, the switch body 212, and the collimator body 213 are perpendicular to the circular surface of the ring structure, and are perpendicular to the center of the ring structure. When each of the circular gratings detects that the rotation of the source body 211, the switch body 212, and the collimator body 213 of the radiotherapy equipment rotationally deviates, an alarm signal is sent to the controller 230 so that the controller 230 obtains the rotational deviation amount according to the detector 220. The rotational deviation amount which is used to recover the normal rotation movement of the deviated rotational loads, is calculated by the corresponding driving unit in the driving apparatus 240.

Different from conventional arts, the device for controlling the rotation of radiotherapy equipment according to the present disclosure monitors the actual position of the source body, the collimator, and the switch body of the rotating gamma head knife. The deviation of the rotation axis is detected during the synchronous or asynchronous rotation. As such, by monitoring the actual rotation of the rotating part of the radiotherapy equipment, it is timely corrected when the rotation of any one of the source body, the collimator, and the switch body rotationally deviates, thereby improving the safety and positioning accuracy of the radiotherapy equipment.

Figure 3:
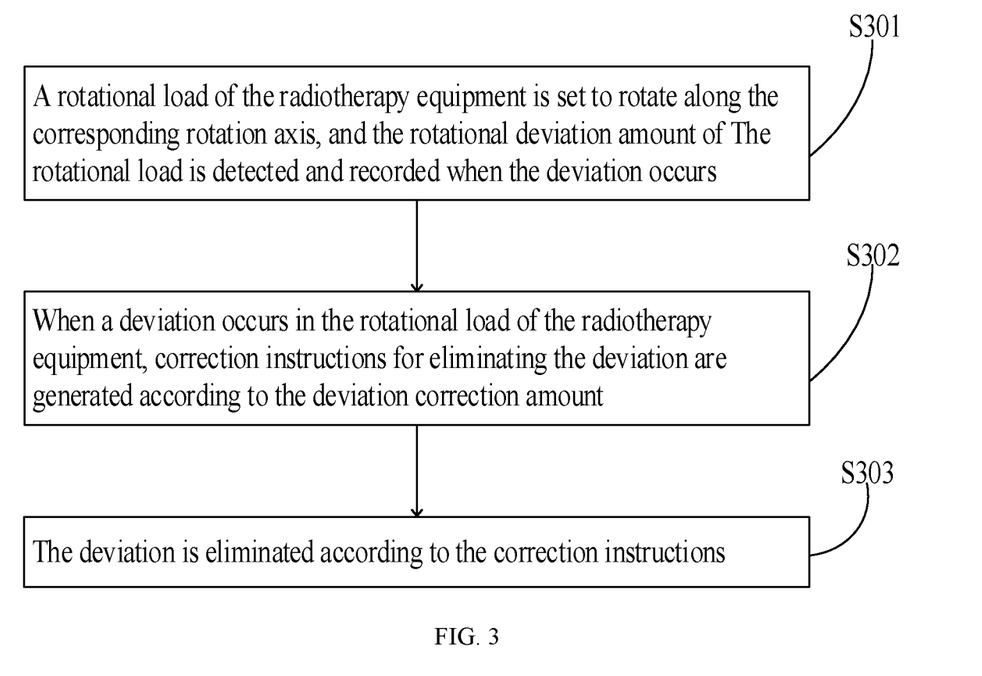
FIG. 3 is a schematic flowchart of a method for controlling the rotation of radiotherapy equipment, according to a first embodiment of the present disclosure.

Referring to FIG. 3, FIG. 3 is a schematic flowchart of a method for controlling the rotation of radiotherapy equipment, according to a first embodiment of the present disclosure. The method includes operations of S301 to S303.

In step S301, the rotational loads of the radiotherapy equipment are set to rotate along the corresponding rotation axis, and the rotational deviation amount of each rotational load is detected and recorded when the deviation occurs.

During a normal operation of the radiotherapy equipment, the source body, the switch body and the collimator body are in a bowl-shaped structure, and are sequentially placed and covered with one on another and controlled by different driving motors. The source body, the switch body and the collimator body are rotatable along an axis passing vertically through the bottom of each bowl structure while allowing relative rotation therebetween. Only by accurate controlling of the rotation of the source body, the switch body, and the collimator body, effective treatment is performed. In the present disclosure, it is possible to accurately control the radioactive source to be opened or closed in the radiotherapy equipment according to a predetermined treatment plan, reducing harm to the medical personnel and the healthy tissue of the patient.

During the operation of the source body, the switch body, and the collimator body, rotation of the three is monitored or detected by a circular grating, and the circular grating is a ring structure. Since the source body, the switch body, and the collimator body are sequentially covered, in an ideal state, the rotation shafts along which the respective rotations coincide on the same straight line. The straight line is set to be perpendicular to the circular surface of the circular grating ring structure and passes through the center of the circle surface. The process proceeds to operation S302.

In operation S302, when a deviation occurs in at least one of the rotational loads of the radiotherapy equipment, correction instructions for eliminating the deviation are generated according to the rotational deviation amount.

The position of the circular grating is fixed, and when it is detected that the relative positions of the rotation axis of the source body, the switch body and the collimator body and the circular grating change, for example, the rotation axis of the rotation shafts of the source body, the switch body or the collimator body is no longer perpendicular to the circular surface of the ring structure of the circular grating, or the rotation axis is not perpendicularly passing through the center of the circular surface, it is determined that the rotation of the source body, the switch body, or the collimator body rotationally deviates, from normal operation and needed to be corrected. After the rotational deviation amount is calculated by the circular grating, correction instructions are generated according to the rotational deviation amount. The correction instructions are instructions for eliminating the deviation and the correction instructions include a correction mechanism that is determined by comparing the rotational deviation amount of the rotation axis relative to the circular grating to the preset position of the rotation axis relative to the circular grating. After the correction instructions are sent, the process proceeds to operation S303.

In operation S303, the deviated rotational load(s) is driven to move according to the correction instructions until the deviation is eliminated.

After the correction instructions are issued, the driving motor that drives the source body, the switch body, and the collimator body rotates to eliminate deviation that occurs during the rotation of the source body, the switch body, and the collimator body according to the deviation correction amount in the correction instructions, resuming the work of the radiotherapy equipment back to normal.

Different from the conventional arts, the method for controlling the rotation of radiotherapy equipment according to the present disclosure performs actual position monitoring on the rotation of the source body, the collimator, and the switch body of the gamma head knife rotating equipment. The deviation for the corresponding rotation shaft is detected during the synchronous or asynchronous rotation. As such, by monitoring the actual rotation of the rotating part of the radiotherapy equipment, it is timely corrected when the rotation of any one of the source body, the collimator, and the switch body rotationally deviates, thereby improving the safety and positioning accuracy of the radiotherapy equipment.

Figure 4:
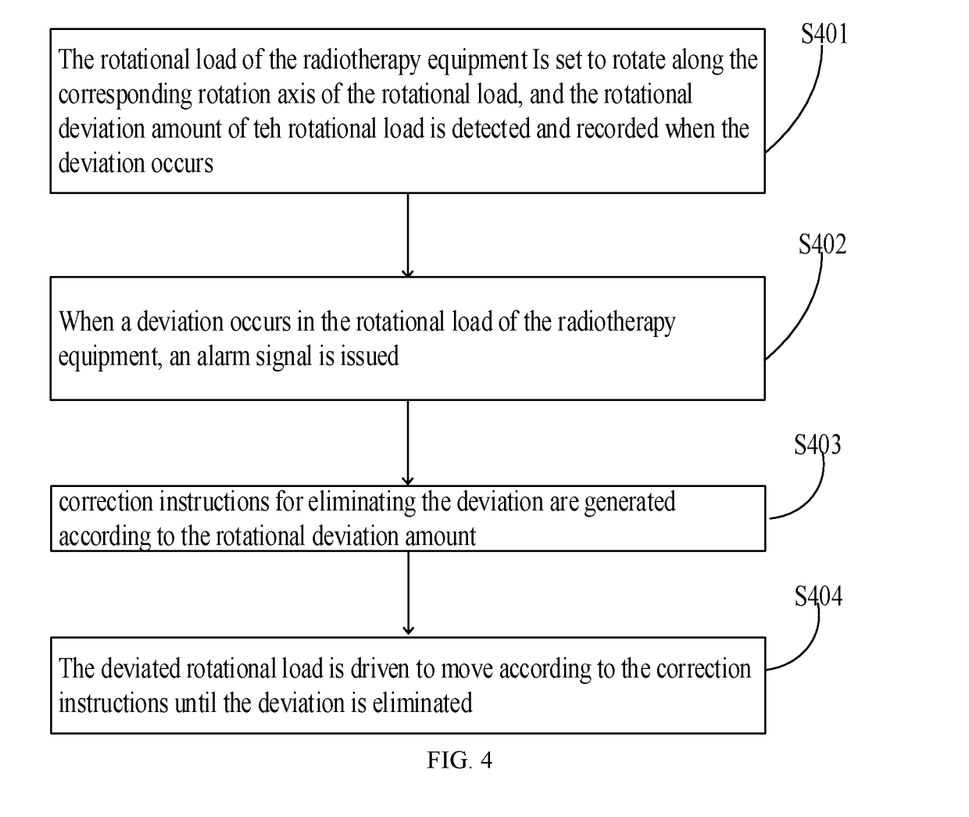
FIG. 4 is a schematic flowchart of a method for controlling the rotation of radiotherapy equipment, according to a second embodiment of the present disclosure.

Referring to FIG. 4, FIG. 4 is a schematic flowchart of a method for controlling the rotation of radiotherapy equipment, according to a second embodiment of the present disclosure. The method includes operations of S401 to S404.

In operation S401, the rotational loads of the radiotherapy equipment are set to rotate along the corresponding rotation shaft, and the rotational deviation amount of each rotational load is detected and recorded when the deviation occurs.

This operation is same as the previous embodiment of FIG. 3 and will not be described again. Similarly, after the radiotherapy equipment enters operation, the process proceeds to operation S402.

In operation S402, when a deviation occurs in at least one of the rotational loads of the radiotherapy equipment, an alarm signal is issued.

Similar to the previous embodiment, a circular grating is used to monitor the rotation of the source body, the switch body, and the collimator body of the radiotherapy equipment. The circular grating monitors the relative position of the reference rotation axis to the rotation axis of the rotation shafts along which the source body, the switch body, and the collimator body rotate. And when the rotation of the source body, the switch body, and the collimator body deviates, the position or angle of the rotation shafts thereof with respect to the circular grating is changed undoubtedly. After the deviation is determined, the circular grating determines the type of the deviation and calculates the rotational deviation amount, and sends the alarm signal to the controller. The process continues to operation S403.

In operation S403, correction instructions for eliminating the deviation are generated according to the rotational deviation amount.

Alarm signal is parsed after being received. The rotational deviation amount carried therein is obtained, and the correction instructions are generated based on the rotational deviation amount. The correction instructions are instructions for eliminating the deviation for any one or more of the source body, the switch body, and the collimator body, and include a deviation correction amount required for restoring the normal rotation (for example, restoring to the position parallel to or overlapping with the reference rotation axis). The deviation correction amount is incorporated into the correction instructions and the correction instructions are sent to a driving motor.

In operation S404, the deviated rotational load(s) is driven to move according to the correction instructions until the deviation is eliminated.

After the correction instructions are issued, the driving motor that drives the source body, the collimator body, and the switch body rotates to eliminate the deviation that occurs during the rotation of the source body, the collimator body, and the switch body, according to the deviation correction amount carried in the correction instructions, resuming the work of the radiotherapy equipment back to normal.

Different from conventional arts, the method for controlling the rotation of radiotherapy equipment according to the present disclosure monitors the actual rotation position of the source body, the collimator, and the switch body of the gamma head knife. The deviation of the corresponding rotation axis of the rotation shafts is detected during the synchronous or asynchronous rotation. As such, by monitoring the actual rotation of the rotating part of the radiotherapy equipment, it is timely corrected when the rotation of any one of the source body, the collimator, and the switch body rotationally deviates, thereby improving the safety and positioning accuracy of the radiotherapy equipment.

In the above-mentioned embodiments, the source body, the switch body, and the collimator body are all bowl-shaped structures. Of course, the source body, the switch body, and the collimator body may also be in other shapes, such as ring shapes or trumpet shapes.

Figure 5:
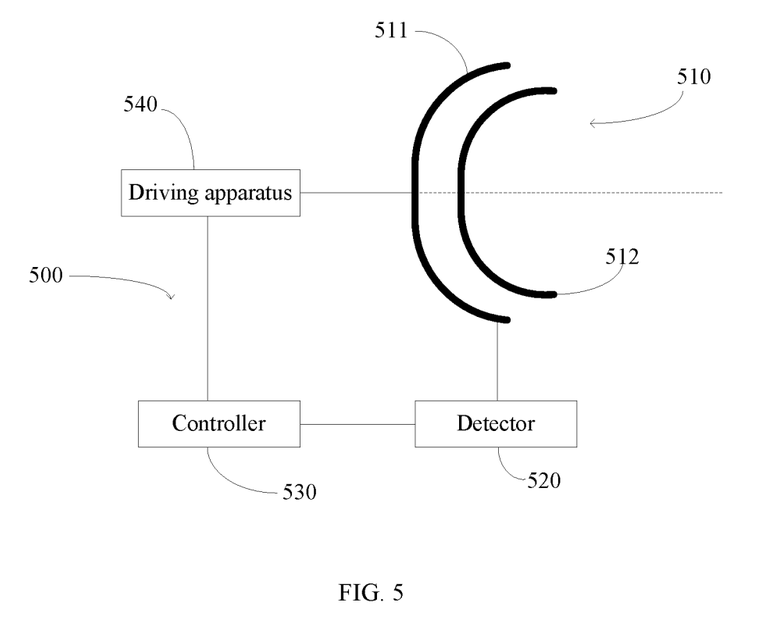
FIG. 5 is a schematic structural diagram of a device for controlling the rotation of radiotherapy equipment, according to a third embodiment of the present disclosure.

In another embodiment, FIG. 5 is a schematic structural diagram of a device for controlling the rotation of radiotherapy equipment, according to a third embodiment of the present disclosure. The device 500 includes a detector 520, a controller 530, and a driving apparatus 540. Combining with rotational loads 510 of the radiotherapy equipment (not shown), a full-closed loop structure is formed.

Referring to FIG. 5, the rotational loads 510 include a source body 511 and a collimator body 512 in sequence from outside to inside, but do not include a switch body. The source body 511 and the collimator body 512 are rotatable synchronously or asynchronously along a rotation shaft. The detector 520 is connected to the rotational loads 510 to monitor the rotation of the source body 511 and the collimator body 512. When the source body 111 or/and the switch body 511 rotationally deviates during rotation, rotational deviation amount is monitored/detected by the detector 520 immediately. The detector 520 sends the controller 530 the rotational deviation amount of the source body 511 or/and the collimator body 512 when occurs. The controller 530 calculates a deviation correction amount required for normal rotation according to the detected rotational deviation amount, and further sends correction instructions to the driving apparatus 540. The driving apparatus 540 is configured to drive each component of the rotational loads to rotate in a normal state, and correct the rotation of a deviated component according to the correction instructions, to perform a normal rotation.

Figure 6:
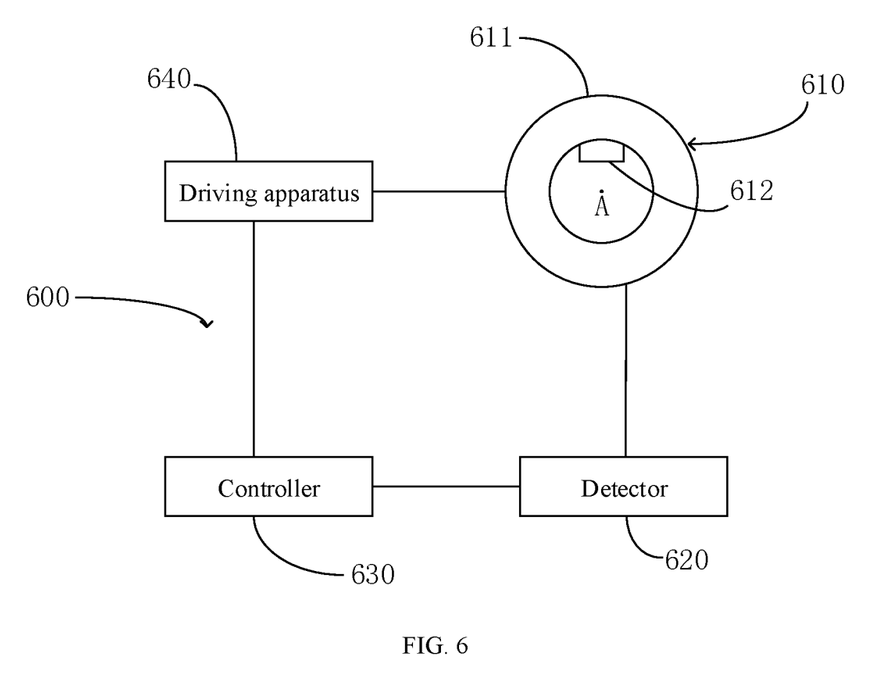
FIG. 6 is a schematic structural diagram of a device for controlling the rotation of radiotherapy equipment, according to a fourth embodiment of the present disclosure.

In essence, the rotational load may also be a rotational gantry rotatable about a rotation axis. FIG. 6 is a schematic structural diagram of a device for controlling the rotation of radiotherapy equipment, according to a fourth embodiment of the present disclosure. The device 600 includes a detector 620, a controller 630, and a driving apparatus 640. Combining with a rotational load 610 of the radiotherapy equipment (not shown), a full-closed loop structure is formed.

Referring to FIG. 6, the rotational load 610 includes a rotational gantry 611, and a treatment head 612 is disposed on the rotational gantry 611. When the rotational gantry 611 rotates about a rotation axis A, the treatment head 612 can be driven to rotate together. The detector 620 is connected to the rotational load 610 to detect the rotation of the rotational gantry 611, and record a rotational deviation amount when the rotational gantry 611 rotationally deviates. The controller 630 is configured to generate correction instructions according to the recorded rotational deviation amount when the detector 620 detects that the rotational gantry 611 rotationally deviates, and send the driving apparatus 640 the correction instructions. The driving apparatus 640 is configured to drive the deviated rotational gantry 611 to move according to the correction instructions issued by the controller 630 until the deviation is eliminated.

The rotational gantry 611 may include an annular gantry (also referred to as a drum) as shown in FIG. 6, and may also include a C-arm gantry and the like.

The detector may also be an encoder, which is not specifically limited here, as long as it can detect the rotational deviation amount of the rotational load.

Figure 7:
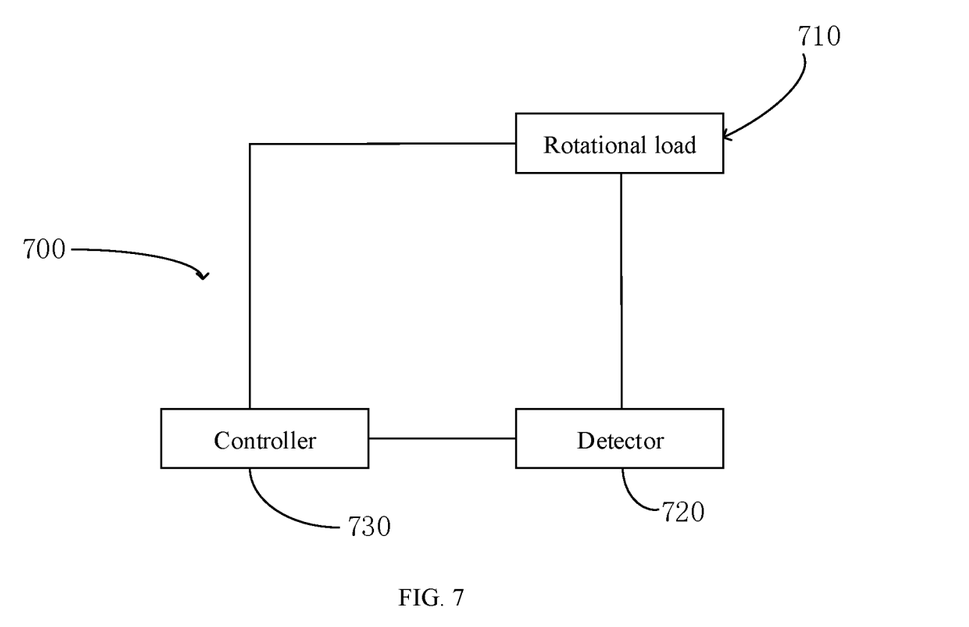
FIG. 7 is a schematic structural diagram of a device for controlling the rotation of radiotherapy equipment, according to a fifth embodiment of the present disclosure.

In order to simplify the device for controlling the rotation of radiotherapy equipment, the drive of the radiotherapy equipment itself can be used to drive the rotational load so as to eliminate the deviation. FIG. 7 is a schematic structural diagram of a device for controlling the rotation of radiotherapy equipment, according to a fifth embodiment of the present disclosure. The device 700 includes a detector 720 and a controller 130. Combining with a rotational load 710 of the radiotherapy equipment (not shown), a full-closed loop structure is formed. The detector 720 is configured to detect the rotation of the rotational load 710 of the radiotherapy equipment, and record a rotational deviation amount when the rotational load 710 rotationally deviates. The controller 730 is configured to generate correction instructions for eliminating the deviation according to the recorded rotational deviation amount when the detector 720 detects that the rotational load 710 of the radiotherapy equipment rotationally deviates, restoring the normal rotation of the rotational load 710 of the radiotherapy equipment.

The device for controlling the rotation of radiotherapy equipment in the embodiments of the present disclosure monitors the actual rotation of the rotational load of the radiotherapy equipment and timely instructs the radiotherapy equipment to correct the rotational load, when the rotation of the rotational load rotationally deviates, to improve the safety and positioning accuracy of the radiotherapy equipment.

Figure 8:
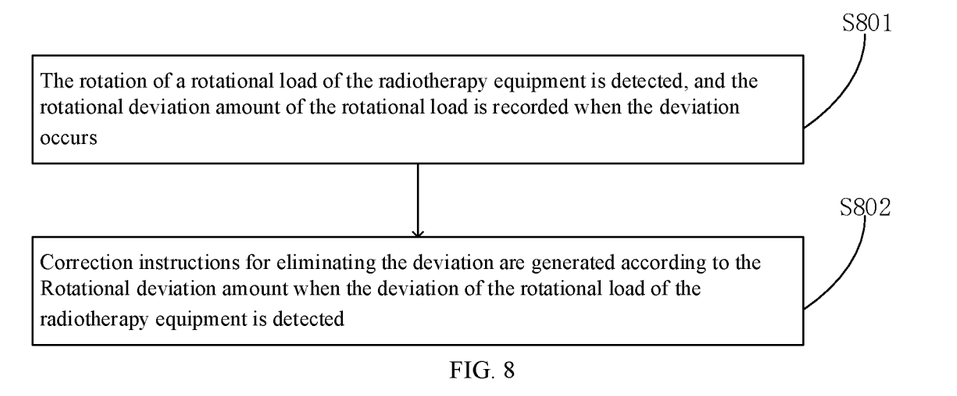
FIG. 8 is a schematic flowchart of a method for controlling the rotation of radiotherapy equipment, according to a third embodiment of the present disclosure.

FIG. 8 is a schematic flowchart of a method for controlling the rotation of radiotherapy equipment, according to a third embodiment of the present disclosure. The method includes operations of S801 and S802.

In operation S801, the rotation of a rotational load of the radiotherapy equipment is detected, and the rotational deviation amount of the rotational load is recorded when the deviation occurs.

The device for controlling the rotation of radiotherapy equipment detects the rotation of the rotational load of the radiotherapy equipment, and records the rotational deviation amount of the rotational load when the deviation occurs.

Here, the rotational load may include: a source body, a switch body, and a collimator body; or a source body and a collimator body; or a rotational gantry which may be an annular gantry or a C-arm gantry.

Here, the rotational deviation amount includes at least one of positional deviation and angular deviation.

In operation S802, correction instructions for eliminating the deviation are generated according to the rotational deviation amount when the deviation of the rotational load of the radiotherapy equipment is detected.

When detecting that the rotational load of the radiotherapy equipment rotationally deviates, the control device generates correction instructions according to the rotational deviation amount. The correction instructions can instruct the drive of the radiotherapy equipment itself to eliminate the deviation of the rotational load, thereby resuming the work of the rotational load of the radiotherapy equipment back to normal, and improving the safety and positioning accuracy of the radiotherapy equipment.

Before operation S801, the method may further include that: the rotation axis of the rotational loads is controlled to be parallel to or overlapped with a reference rotation axis. Through the reference rotation axis, the rotation axis of the rotational loads is respectively disposed parallel to the reference rotation axis, and are eventually parallel to or even overlapped with each other, so that the rotation of the rotational loads is more accurate.

An embodiment of the present disclosure provides a device for controlling the rotation of radiotherapy equipment. The device may include a processor and a memory, and the memory stores instructions that may be loaded and executed by the processor to implement the method for controlling the rotation of radiotherapy equipment according to any one of the foregoing embodiments.

In addition, an embodiment of the present disclosure provides a storage medium storing instructions that, when the storage medium runs on a processing unit, may cause the processing unit to perform the method for controlling the rotation of radiotherapy equipment according to any one of the foregoing embodiments.

The foregoing description is merely embodiments of the present disclosure, and does not limit the scope of the present disclosure. Any equivalent structure or equivalent process transformation using the description of the present disclosure and the accompanying drawings are directly or indirectly applied to other related technologies shall fall within the protection scope of the present disclosure.

What is claimed is:

1. A device for controlling rotation of radiotherapy equipment, to control rotation of the radiotherapy equipment about a rotation axis, wherein the device comprises:

a detector, configured to detect the rotation of a rotational load of the radiotherapy equipment, and record a rotational deviation amount when the rotational load rotationally deviates; and a controller, configured to generate correction instructions for eliminating deviation of the rotational load according to the rotational deviation amount when the detector detects the rotational load of the radiotherapy equipment rotationally deviates.

2. The device for controlling the rotation of radiotherapy equipment according to claim 1, wherein the detector further comprises:

a detection unit, configured to detect the rotation of the rotational load; and an alarm unit, configured to issue an alarm signal according to the rotational deviation amount when the deviation of the rotational load is detected.

3. The device for controlling the rotation of radiotherapy equipment according to claim 2, wherein the controller further comprises:

a receiving unit, configured to receive the alarm signal sent by the detector; and a command unit, configured to generate the correction instructions according to the alarm signal.

4. The device for controlling the rotation of radiotherapy equipment according to claim 3, wherein:

the alarm signal includes the rotational deviation amount when the rotational load rotationally deviates; and the correction instructions include a deviation correction amount calculated by the controller according to the rotational deviation amount, to resume the rotational load that has been deviated to normal rotation.

5. The device for controlling the rotation of radiotherapy equipment according to claim 1, further comprising: a driving apparatus, configured to drive the rotational load that has rotationally deviated to move according to the correction instructions issued by the controller to eliminate the deviation of the rotational load.

6. The device for controlling the rotation of radiotherapy equipment according to claim 1, wherein the deviation of the rotational load is at least one of a positional deviation or an angular deviation.

7. The device for controlling the rotation of radiotherapy equipment according to claim 1, wherein the detector is a circular grating or an encoder.

8. The device for controlling the rotation of radiotherapy equipment according to claim 1, wherein the controller is configured to further control rotation axis of the rotational load to be parallel to or overlapped with a reference rotation axis.

9. The device for controlling the rotation of radiotherapy equipment according to claim 1, wherein the rotational load comprises a plurality of rotational loads, and the rotation of the plurality of rotational loads is synchronous rotation or asynchronous rotation;

the detector is configured to detect the rotation of the plurality of rotational loads of the radiotherapy equipment, and record a rotational deviation amount when at least one of the plurality of rotational loads rotationally deviates; and the controller is configured to generate correction instructions for eliminating the deviation according to the rotational deviation amount when the detector detects at least one of the plurality of rotational loads of the radiotherapy equipment rotationally deviates.

10. The device for controlling the rotation of radiotherapy equipment according to claim 9, wherein the rotational load comprises:

a source body and a collimator body; or, a source body, a switch body, and a collimator body.

11. The device for controlling the rotation of radiotherapy equipment according to claim 1, wherein the rotational load comprises a rotational gantry.

12. A method for controlling the rotation of radiotherapy equipment, comprising:

detecting rotation of a rotational load of the radiotherapy equipment, and recording a rotational deviation amount when the rotational load rotationally deviates; and generating correction instructions for eliminating deviation of the rotational load according to the rotational deviation amount when the deviation of the rotational load has been detected.

13. The method for controlling the rotation of radiotherapy equipment according to claim 12, wherein the generating correction instructions for eliminating the deviation according to the rotational deviation amount when the deviation of the rotational load has been detected comprises:

issuing an alarm signal according to the rotational deviation amount when the deviation of the rotational load of the radiotherapy equipment has been detected; and generating the correction instructions according to the rotational deviation amount in the alarm signal, wherein the correction instructions include a deviation correction amount calculated according to the rotational deviation amount to resume the rotational load that has been deviated to normal rotation.

14. The method for controlling the rotation of radiotherapy equipment according to claim 12, further comprising: driving the rotational load that has been deviated to move according to the correction instructions to eliminate the deviation.

15. The method for controlling the rotation of radiotherapy equipment according to claim 12, wherein the deviation of the rotational load is at least one of a positional deviation or an angular deviation.

16. The method for controlling the rotation of radiotherapy equipment according to claim 12, wherein before detecting the rotation of a rotational load of the radiotherapy equipment, and recording a rotational deviation amount when the rotational load rotationally deviates, the method further comprises: controlling the rotation axis of the rotational load to be parallel to or overlapped with a reference rotation axis.

17. The method for controlling the rotation of radiotherapy equipment according to claim 12, wherein the rotational load comprises a plurality of rotational loads, and the rotation of the plurality of rotational loads is synchronous rotation or asynchronous rotation;

the detecting the rotation of a rotational load of the radiotherapy equipment, and recording a rotational deviation amount when the rotational load rotationally deviates comprises: detecting the rotation of the plurality of rotational loads of the radiotherapy equipment, and recording a rotational deviation amount when at least one of the plurality of rotational loads rotationally deviates; and the generating correction instructions for eliminating deviation of the rotational load according to the rotational deviation amount when the deviation of the rotational load has been detected comprises: generating correction instructions for eliminating the deviation of the plurality of rotational loads according to the rotational deviation amount when the deviation of at least one of the plurality of rotational loads of the radiotherapy equipment is detected.

18. The method for controlling the rotation of radiotherapy equipment according to claim 12, wherein the rotational load comprises:

a source body and a collimator body; or, a source body, a switch body, and a collimator body.

19. The method for controlling the rotation of radiotherapy equipment according to claim 12, wherein the rotational load comprises a rotational gantry.

20. A device for controlling the rotation of radiotherapy equipment, comprising a processor and a memory, wherein the memory stores instructions that are loaded and executed by the processor to implement the method for controlling the rotation of the radiotherapy equipment according to claim 12.

* * * * *